(12) United States Patent
Ozminkowski, Jr.

(10) Patent No.: US 10,238,053 B2
(45) Date of Patent: Mar. 26, 2019

(54) HYBRID TOMATO VARIETY H1546

(71) Applicant: H.J. Heinz Company Brands LLC, Pittsburgh, PA (US)

(72) Inventor: Richard Henry Ozminkowski, Jr., Lodi, CA (US)

(73) Assignee: H.J. Heinz Company Brands LLC, Pittsburgh, PA (US)

( * ) Notice: Subject to any disclaimer, the term of this patent is extended or adjusted under 35 U.S.C. 154(b) by 0 days.

(21) Appl. No.: 15/669,135

(22) Filed: Aug. 4, 2017

(65) Prior Publication Data
US 2018/0035634 A1    Feb. 8, 2018

Related U.S. Application Data

(60) Provisional application No. 62/371,459, filed on Aug. 5, 2016.

(51) Int. Cl.
*A01H 5/10*   (2018.01)
*A01H 5/08*   (2018.01)

(52) U.S. Cl.
CPC .................. *A01H 5/08* (2013.01); *A01H 5/10* (2013.01)

(58) Field of Classification Search
None
See application file for complete search history.

(56) References Cited

U.S. PATENT DOCUMENTS 7,910,811 B2 *   3/2011   Ramon .................... A01H 5/08
                                                          435/411

* cited by examiner

*Primary Examiner* — Jason Deveau Rosen
(74) *Attorney, Agent, or Firm* — Fitch, Even, Tabin & Flannery LLP

(57) ABSTRACT

Hybrid tomato variety 'H1546' is described. The 'H1546' tomato variety is a field-culture hybrid tomato variety suitable for machine harvest.

13 Claims, 1 Drawing Sheet
(1 of 1 Drawing Sheet(s) Filed in Color)

US 10,238,053 B2

HYBRID TOMATO VARIETY H1546

CROSS REFERENCE TO RELATED APPLICATION

This application claims the benefit of U.S. Provisional Application No. 62/371,459, filed Aug. 5, 2016, which is incorporated by reference herein in its entirety.

FIELD

This invention relates to the field of plant breeding. In particular, this invention relates to a new tomato, *Solanum lycopersicum*, variety denominated 'H1546'.

BACKGROUND

Breeding improved tomato varieties involves providing genetics that give an advantage to the grower, processor, consumer, or other member of the supply chain. The improvement may be in the form of field performance, disease resistance, factory performance, or a fruit quality characteristic. For a tomato variety to be suitable to be grown for processing, the variety must have a concentrated fruit setting and maturity, firm fruit, and sufficient rot tolerance to allow early fruit to remain rot-free while later fruit continues to develop and ripen.

Most commercial processing tomato varieties are hybrids resulting from a cross pollination of two true-breeding, inbred parents. Through the use of true-breeding lines, a hybrid is produced that often displays characteristics of each parent, and often demonstrates characteristics that are superior to either parent alone, or that allow a hybrid to mask inadequacies of the individual parents.

Processing tomato varieties combining high levels of tolerance to bacterial canker (*Clavibacter michiganense* ssp. *michiganense*), early blight (*Alternaria solani*), late blight (*Phytophthora infestans*), and bacterial spot (*Xanthomonas* spp.) are highly desirable in humid climates where these diseases present production issues.

Moreover, combining resistance to tomato spotted wilt virus (TSWV) and race 3 of *Fusarium oxysporum* f.sp. *lycopersici* in tomato varieties adapted to arid climates is desirable to the processing industry in California and other global tomato processing regions where these diseases limit production. Further, *Fusarium oxysporum* f.sp. *lycopersici* race 3 (*Fusarium* 3) is a growing problem in the California tomato growing region and in other production areas worldwide, such as the Dominican Republic and Mexico. Productive, adapted varieties have been in demand by growers and processors since the mid 1990's with resistance to this pathogen. The disease has become a major limiting factor in tomato production in some California fields. Growers and processors need a range of tomato varieties with *Fusarium* 3 resistance, since products specifications vary with respect to juice viscosity, soluble solids content, field storage, and general field adaptability. Thus, varieties with resistance to either or both TSWV and *Fusarium* 3 are in high demand by both growers and processors to ensure a productive crop cycle.

An additional important contribution that tomatoes provide to the human diet is the antioxidant lycopene. Specifically, processing tomato varieties are the key form of tomato intake in the US diet. Higher levels of lycopene are beneficial both from a nutritional standpoint and from a consumer perception and quality standpoint. Tomato varieties having higher levels of lycopene result in products with a deeper red color that can be considered an indicator of higher product quality. Thus, a tomato variety with higher levels of lycopene, and improved color in general, can be valuable from both a nutritional standpoint and a quality standpoint. However, to be commercially viable and useful, the tomato variety must perform acceptably in the field and factory, as required by any other processing tomato variety. Previous varieties with increased lycopene levels have shown severe reductions in fruit quality, firmness, yield, and a sensitivity to fruit rots.

SUMMARY

In order to meet these needs, the present disclosure provides improved tomato variety 'H1546', a late season variety with very thick hot-break juice viscosity. 'H1546' is a solid-fleshed variety, without the semi-liquid gel that is normally found in tomato fruit locules; fruit size has averaged 73 grams. 'H1546' carries resistance to *verticillium* wilt race 1, *Fusarium* wilt races 1 and 2, southern root knot nematode, and has good tolerance to fruit rot. The foliage of 'H1546' has also expressed intermediate resistance to early blight (*Alternaria solani*) and bacterial spot (*Xanthamonas* spp.) in trials grown in Ontario, Canada.

The characteristics that determine the quality of tomato fruit used for processing are different from that of tomato fruit used for the fresh market. Processing characteristics are commonly tested on samples of tomato pulp or juice produced in a way that is well known in the art. For example, a fixed mass of tomatoes may be cooked in a microwave oven for several minutes to halt any enzymatic breakdown of the sample, lost water is replaced, and the sample is pulped to remove skin and seeds to produce a uniform juice sample. The juice sample can be analyzed for various quality parameters important to processing tomato including, but not limited to, gross viscosity measurements such as juice Bostwick, soluble solids measurements using a refractometer (° Brix), measurements of acidity and pH, and measurements of color via a Hunter a/b score. The Hunter a/b score is an international industry and USDA standard color measurement of tomato products that provides a representation of the color of the product in a single dimensionless unit. The "a" value represents color on the green to red dimension whereas "b" represents the blue to yellow dimension; a higher a/b ratio is associated with more red color and is often considered a superior product.

Tomato varieties contain varying levels of lycopene (Garcia and Barrett, 2006). Lycopene content of tomato juice can be measured using a protocol developed by Anthon and Barrett (2001), which involves an ethanol/hexane extraction followed by quantification using reflectance at 503 nm.

As used herein, tomato variety 'H1546', tomato plant 'H1546', tomato seed 'H1546', and 'H1546' all refer to the hybrid tomato variety 'H1546', and parts and seeds thereof, having ATCC Accession Number PTA-124279.

Accordingly, in one embodiment, the present disclosure is directed to tomato seed designated as 'H1546' having ATCC Accession Number PTA-124279. In one embodiment, the present disclosure is directed to a tomato plant and parts isolated therefrom produced by growing 'H1546' tomato seed. In another embodiment, the present disclosure is directed to a tomato plant and parts isolated therefrom having all the physiological and morphological characteristics of a tomato plant produced by growing 'H1546' tomato seed having ATCC Accession Number PTA-124279. In still another embodiment, the present disclosure is directed to an $F_1$ hybrid tomato seed, plants grown from the seed, and leaves, ovules, pollen, fruit, cotyledons, embryos, meristems, anthers, roots, root tips, pistils, flowers, stems, calli, stalks, hypocotyls, and pericarps isolated therefrom having 'H1546' as a parent, wherein 'H1546' is grown from 'H1546' tomato seed having ATCC Accession Number PTA-124279.

Tomato plant parts include leaves, ovules, pollen, fruit, cotyledons, embryos, meristems, anthers, roots, root tips, pistils, flowers, stems, calli, stalks, hypocotyls, pericarps, and the like. In another embodiment, the present disclosure is further directed to tomato fruit, stems, leaves, parts of leaves, roots, root tips, pollen, ovules, and flowers isolated from 'H1546' tomato plants. In another embodiment, the present disclosure is further directed to tissue culture or cells derived from 'H1546' tomato plants.

In yet another embodiment, the present disclosure is further directed to a method of selecting tomato plants by a) growing 'H1546' tomato plants wherein the 'H1546' plants are grown from tomato seed having ATCC Accession Number PTA-124279; and b) selecting a plant from step a). In another embodiment, the present disclosure is further directed to tomato plants, plant parts and seeds produced by the tomato plants, where the tomato plants are isolated by the selection method of the disclosure.

In another embodiment, the present disclosure is further directed to a method of breeding tomato plants by crossing a tomato plant with a plant grown from 'H1546' tomato seed having ATCC Accession Number PTA-124279. In still another embodiment, the present disclosure is further directed to tomato plants, tomato parts from the tomato plants, and seeds produced therefrom where the tomato plant is isolated by the breeding method of the disclosure.

BRIEF DESCRIPTION OF THE DRAWINGS

The patent or application file contains at least one drawing executed in color. Copies of this patent or patent application publication with color drawings will be provided by the office upon request and payment of the necessary fee.

The FIGURE illustrates fruit and general plant structure of tomato variety 'H1546'.

DETAILED DESCRIPTION

Comparison of Variety to Closest Varieties

Data in the following tables (Tables 1-4) are based primarily upon trials conducted in Collegeville, Calif., from two replications, non-staked, in a research plot environment. Comparisons among varieties for processing traits were done over two years of side-by-side testing throughout California. Disease resistance and adaptability assessments are based upon numerous observations collected throughout California and in regions and climates with specific disease pressures for ripe fruit rots, bacterial spot, bacterial canker, early blight, and late blight, including Ontario, Canada.

'H1546' Tomato Variety

Described herein is a new and distinct tomato variety named 'H1546'. Tomato plants of 'H1546' are well adapted to both humid and arid climates. The plants are resistant to *verticillium* wilt race 1, *fusarium* wilt races 1 and 2, and southern root knot nematode, with intermediate resistances to bacterial spot and late blight. High yields produce fruit that are medium-sized for a processing tomato (73 grams). When cut laterally, the fruit are solid; no gel forms amongst the seed. Hot-break juice has a very thick viscosity and a low soluble solids content.

The tomato variety 'H1546' is uniform and stable within commercially acceptable limits. As is true with other tomato varieties, a small percentage of variants can occur within commercially acceptable limits for almost any characteristic during the course of repeated multiplication. However, no variants were observed during the two years in which the variety was observed to be uniform and stable.

TABLE 1

Characterization of the 'H1546' tomato variety

|  | 'H1546' | Check Variety 'H5608' | Check Variety 'H3402' |
|---|---|---|---|
| Seedling | | | |
| Anthocyanin in hypocotyl | Present | Present | Present |
| Habit of 3-4 week seedling | Normal | Normal | Normal |
| Mature Plant | | | |
| Height (cm) | 47 | 54 | 44 |
| Growth Type | Determinate | Determinate | Determinate |
| Form | Compact | Compact | Sprawling |
| Size of Canopy | Large | Large | Large |
| Habit | Sprawling | Sprawling | Sprawling |
| Stem | | | |
| Branching | Profuse | Profuse | Profuse |
| Branching at Cotyledon | Absent | Absent | Absent |
| # Nodes below first inflorescence | 4-7 | 4-7 | 4-7 |
| # Nodes between early inflorescences (1st-2nd) | 2 | 1-2 | 1-2 |
| # Nodes between later inflorescence | 1-2 | 1-2 | 1-2 |
| Pubescence on younger stems | Moderately hairy | Sparsely hairy | Moderately hairy |
| Leaf | | | |
| Type | | | |
| Morphology | Tomato Compound with major and minor leaflets | Tomato Compound with major and minor leaflets | Tomato Compound with major, minor, and subminor leaflets |
| Margins of major leaflets | Nearly entire | Nearly entire | Nearly entire |
| Marginal rolling or wiltiness | Slight | Moderate | Moderate |
| Onset of leaflet rolling | Midseason | Midseason | Midseason |
| Surface of major leaflets | Smooth | Rugose | Rugose |
| Pubescence | Normal | Normal | Normal |
| Inflorescence | | | |
| Type | Simple | Forked | Forked |
| Average # flowers in inflorescence | 5 | 5 | 5 |
| Leafy or "running" inflorescence | Absent | Absent | Absent |
| Flower | | | |
| Calyx | Normal | Normal | Normal |
| Calyx-Lobes | Shorter than corolla | Shorter than corolla | Shorter than corolla |
| Corolla Color | Yellow | Yellow | Yellow |
| Style pubescence | Sparse | Sparse | Sparse |
| Anthers | Fused/Tubed | Fused/Tubed | Fused/Tubed |
| Fasciation | Absent | Absent | Absent |
| 1st flower of 2nd or 3rd Inflorescence | Absent | Absent | Absent |
| Fruit | | | |
| Typical shape | Blocky oval | Blocky oval | Blocky oval |
| Shape of transverse | Angular | Round | Round |

TABLE 1-continued

Characterization of the 'H1546' tomato variety

| | 'H1546' | Check Variety 'H5608' | Check Variety 'H3402' |
|---|---|---|---|
| section | | | |
| Shape of stem end | Indented | Indented | Flat |
| Shape of blossom end | Indented | Flat | Flat |
| Shape of pistil scar | Dot | Dot | Dot |
| Abscission layer | Absent | Absent | Absent |
| Point of detachment | At calyx | At calyx | At calyx |
| Length of mature fruit (cm) | 6.5 | 5.2 | 5.1 |
| Diameter of fruit at widest point (cm) | 4.3 | 3.8 | 3.5 |
| Weight of mature fruit (g) | 73 | 73 | 60 |
| # Locules | 2-4 | 2-4 | 2-4 |
| Fruit surface | Slightly rough | Smooth | Smooth |
| Fruit base color (mature green stage) | Medium green | Light grey-green | Medium green |
| Fruit pattern (mature green stage) | Uniform | Uniform | Uniform |
| Fruit color (fully ripe) | Red | Red | Red |
| Flesh color (fully ripe) | Red | Red | Red |
| Flesh color | Uniform | Uniform | Uniform |
| Locular gel color of table-ripe fruit | n/a | Yellow | Yellow |
| Ripening pattern | Uniform | Uniform | Uniform |
| Ripening direction | Uniformly | Uniformly | Uniformly |
| Stem scar size | Small | Small | Small |
| Core | Present | Coreless | Coreless |
| Epidermis color | Yellow | Yellow | Yellow |
| Epidermis | Normal | Normal | Normal |
| Epidermis texture | Tough | Tough | Tender |
| Thickness of pericarp (mm) | 8 | 8 | 7 |

TABLE 2

Disease and pest reaction of the 'H1546' tomato variety

| | 'H1546' | Check Variety 'H5608' | Check Variety 'H3402' |
|---|---|---|---|
| Viral Diseases | | | |
| Tomato Spotted Wilt | Susceptible | Resistant | Susceptible |
| Bacterial Diseases | | | |
| Bacterial Canker (*Clavibacter michiganense*) | Susceptible | Susceptible | Intermediately resistant |
| Bacteria Speck (*Pseudomonas* tomato) | Resistant | Resistant | Resistant |
| Bacterial Spot (*Xanthomonas* spp) | Intermediately resistant | Susceptible | Susceptible |
| Bacterial Wilt (*Ralstonia solancearum*) | Susceptible | Susceptible | Susceptible |
| Fungal Diseases | | | |
| Anthracnose (*Collectotrichum* spp.) | Susceptible | Susceptible | Susceptible |
| Brown Root Rot or Corky Root (*Pyrenochaeta lycopersici*) | Susceptible | Susceptible | Susceptible |
| Collar Rot or Stem Canker (*Alternaria solani*) | Intermediately resistant | Susceptible | Susceptible |
| Early Blight Defoliation (*Alternaria solani*) | Intermediately resistant | Susceptible | Susceptible |
| *Fusarium* Wilt Race 1 (*F. oysporum f. lycopersici*) | Resistant | Resistant | Resistant |
| *Fusarium* Wilt Race 2 (*F. oysporum f. lycopersici*) | Resistant | Resistant | Resistant |
| *Fusarium* Wilt Race 3 (*F. oysporum f. lycopersici*) | Susceptible | Susceptible | Susceptible |
| Late Blight, race 0 (*Phytophthora infestans*) | Susceptible | Susceptible | Susceptible |
| *Verticillium* Wilt Race 1 (*V. dahliae* race 1) | Resistant | Resistant | Resistant |
| *Verticillium* Wilt Race 2 (*V. dahliae* race 2) | Susceptible | Susceptible | Susceptible |
| Root Knot Nematode (*M.* sp.) | Resistant | Resistant | Resistant |

TABLE 3

Chemistry and composition of full-ripe fruits of the 'H1546' tomato variety (2 year average, 27 California trials)

| | 'H1546' | Check Variety 'H5608' | Check Variety 'H3402' |
|---|---|---|---|
| Serum viscosity (centistokes) | 10.5 | 11.1 | 8.3 |
| Juice Bostwick (cm) | 10.6 | 10.8 | 13 |
| Soluble solids (°Brix) | 5 | 5 | 5.2 |
| Lycopene (ppm) | 123 | 133 | 117 |
| Hunter a/b (1 year data) | 2.29 | 2.28 | 2.25 |

TABLE 4

Adaptation of the 'H1546' tomato variety

| | 'H1546' | Check Variety 'H5608' | Check Variety 'H3402' |
|---|---|---|---|
| Growth information | | | |
| Fruiting season | Short | Short | Short |
| Relative maturity | Late | Late | Medium |
| Culture | Field | Field | Field |
| Principle use | Concentrated | Whole-pack, Concentrated | Whole-pack, Concentrated |
| Machine harvest | Yes | Yes | Yes |
| Regions of adaptability, by rank | | | |
| California Sacramento Upper/SJ valley | Yes - 1 | Yes - 2 | Yes - 2 |
| California Lower SJ Valley | Yes - 2 | Yes - 1 | Yes - 3 |
| Northeastern USA | Yes - 3 | No | Yes - 1 |

'H1546' can be distinguished from the closest commercial variety, 'H5608' based on fruit characteristics. In particular, while the fruit of 'H1546' has regular locules, the tissue within the locules that normally converts to a gel at maturity remains solid. Moreover, fruit of 'H1546' is less regular than that of 'H5608', making it less amenable to a peeled product. 'H1546' is also a later maturing variety than is 'H5608', and is susceptible to tomato spotted wilt virus. Additionally, 'H1546' is better adapted to more humid climates, such as the Eastern United States than is 'H5608'.

Further Embodiments

Additional methods include, without limitation, chasing selfs. Chasing selfs involves identifying inbred plants among tomato plants that have been grown from hybrid tomato seed. Once the seed is planted, the inbred plants may be identified and selected due to their decreased vigor relative to the hybrid plants that grow from the hybrid seed, or by enzymatic or DNA patterns. By locating the inbred plants, isolating them from the rest of the plants, and self-pollinating them (i.e., "chasing selfs"), a breeder can obtain an inbred line that is identical to an inbred parent used to produce the hybrid.

Accordingly, another aspect of the present disclosure relates to a method for producing an inbred tomato variety by: planting seed of the tomato variety 'H1546'; growing plants from the seed; identifying one or more inbred tomato plants; controlling pollination in a manner which preserves homozygosity of the one or more inbred plants; and harvesting resultant seed from the one or more inbred plants. The step of identifying the one or more inbred tomato plants may further include identifying plants with decreased vigor, i.e., plants that appear less robust than plants of the tomato variety 'H1546'. Tomato plants capable of expressing substantially all of the physiological and morphological characteristics of the parental inbred lines of tomato variety 'H1546' include tomato plants obtained by chasing selfs from seed of tomato variety 'H1546'.

One of ordinary skill in the art will recognize that once a breeder has obtained inbred tomato plants by chasing selfs from seed of tomato variety 'H1546', the breeder can then produce new inbred plants such as by sib-pollinating, or by crossing one of the identified inbred tomato plant with a plant of the tomato variety 'H1546'.

DEPOSIT INFORMATION

A deposit of the tomato variety 'H1546' is maintained by HeinzSeed Company, having an address at 6755 C. E. Dixon, Stockton, Calif. 95206, United States of America. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the American Type Culture Collection, (ATCC), ATCC Patent Depository, 10801 University Boulevard, Manassas, Va., 20110, USA.

At least 2500 seeds of tomato variety 'H1546' were deposited on Jun. 26, 2017 according to the Budapest Treaty in the American Type Culture Collection (ATCC), ATCC Patent Depository, 10801 University Boulevard, Manassas, Va., 20110, USA. The deposit has been assigned ATCC number PTA-124279. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of 30 years, or 5 years after the most recent request, or for the effective life of the patent, whichever is longer, and will be replaced if a deposit becomes nonviable during that period.

What is claimed is:

1. Tomato seed designated as 'H1546', representative sample of seed having been deposited under ATCC Accession Number PTA-124279.

2. A plant produced by growing the seed of claim 1.

3. A plant part from the plant of claim 2.

4. The plant part of claim 3, wherein the part is selected from the group consisting of leaves, ovules, pollen, tomato fruit, cotyledons, meristems, anthers, roots, root tips, pistils, flowers, stems, calli, stalks, hypocotyls, and pericarps.

5. The plant part of claim 3, wherein the part is a tomato fruit.

6. A tomato plant having all the physiological and morphological characteristics of the tomato plant of claim 2.

7. A plant part from the plant of claim 6.

8. The plant part of claim 7, wherein the part is selected from the group consisting of leaves, ovules, pollen, tomato fruit, cotyledons, meristems, anthers, roots, root tips, pistils, flowers, stems, calli, stalks, hypocotyls, and pericarps.

9. The plant part of claim 7, wherein the part is a tomato fruit.

10. Pollen of the plant of claim 2.

11. An ovule of the plant of claim 2.

12. A tissue culture of the plant of claim 2.

13. A method of making tomato seeds comprised of crossing the plant of claim 2 with another tomato plant and harvesting seed therefrom.

* * * * *